(12) United States Patent
Wallace

(10) Patent No.: US 9,996,954 B2
(45) Date of Patent: Jun. 12, 2018

(54) METHODS AND SYSTEMS FOR DYNAMIC DISPLAY OF A TRACE OF A PHYSIOLOGICAL PARAMETER

(71) Applicant: Covidien LP, Mansfield, MA (US)

(72) Inventor: James Wallace, Boulder, CO (US)

(73) Assignee: Covidien LP, Mansfield, MA (US)

( * ) Notice: Subject to any disclaimer, the term of this patent is extended or adjusted under 35 U.S.C. 154(b) by 637 days.

(21) Appl. No.: 14/506,252

(22) Filed: Oct. 3, 2014

(65) Prior Publication Data
US 2015/0099949 A1 Apr. 9, 2015

Related U.S. Application Data

(60) Provisional application No. 61/886,578, filed on Oct. 3, 2013.

(51) Int. Cl.
*A61B 5/1455* (2006.01)
*G06T 11/20* (2006.01)
(Continued)

(52) U.S. Cl.
CPC ........ *G06T 11/206* (2013.01); *A61B 5/14551* (2013.01); *A61B 5/742* (2013.01);
(Continued)

(58) Field of Classification Search
None
See application file for complete search history.

(56) References Cited

U.S. PATENT DOCUMENTS

| 6,684,090 B2 | 1/2004 | Ali et al. |
| 6,996,427 B2 | 2/2006 | Ali et al. |

(Continued)

FOREIGN PATENT DOCUMENTS

| JP | H08-257016 | 10/1996 |
| JP | 2012170748 A | 9/2012 |

(Continued)

OTHER PUBLICATIONS

Allen, "Photoplethysmography and its Application in Clinical Physiological Measurement," Physiol. Meas., vol. 28, pp. R1-R39, Mar. 2007.
Murray et al., "The Peripheral Pulse Wave: Information Overlooked," J. Clin. Monit., vol. 12, pp. 365-377, Sep. 1996.
Shelley, "Photoplethysmography: Beyond the Calculation of Arterial Oxygen Saturation and Heart Rate," Anesth. Analg., vol. 105, pp. S31-S36, Dec. 2007.

*Primary Examiner* — Eric Winakur
*Assistant Examiner* — Marjan Fardanesh

(57) ABSTRACT

Methods and systems are presented for displaying physiological information with a physiological monitor. A physiological parameter, for example oxygen saturation, is computed from a received physiological signal, for example a PPG signal. At least one metric associated with the received physiological signal is determined, for example a statistical measure of uncertainty associated with the determined physiological parameter. Display parameters are determined, for example a width parameter, based on the metrics and a trace of the computed physiological parameter for a subject is displayed. In some embodiments, the width of the displayed trace may be varied based on the width parameter. In some embodiments, additional or alternative characteristics of the displayed trace may be varied based on respective display parameters. The variations in characteristics of the displayed trace may provide dynamic graphical representations of, for example, the uncertainty associated with determined values of the physiological parameter.

24 Claims, 11 Drawing Sheets

(51) Int. Cl.
  *A61B 5/024* (2006.01)
  *A61B 5/00* (2006.01)
  *A61B 5/02* (2006.01)
  *A61B 5/0205* (2006.01)
  *A61B 5/08* (2006.01)

(52) U.S. Cl.
  CPC .............. *A61B 5/02* (2013.01); *A61B 5/0205* (2013.01); *A61B 5/02416* (2013.01); *A61B 5/0816* (2013.01); *A61B 5/7203* (2013.01)

(56) References Cited

U.S. PATENT DOCUMENTS

| | | | |
|---|---|---|---|
| 7,024,233 | B2 | 4/2006 | Ali et al. |
| 8,090,552 | B2 | 1/2012 | Henry et al. |
| 8,260,558 | B2 | 9/2012 | Hayter et al. |
| 8,420,404 | B2 | 4/2013 | Diebold et al. |
| 2001/0031920 | A1* | 10/2001 | Kaufman ............... A61B 5/055 600/431 |
| 2004/0097797 | A1 | 5/2004 | Porges et al. |
| 2008/0091092 | A1 | 4/2008 | Al-Ali |
| 2008/0221418 | A1 | 9/2008 | Al-Ali et al. |
| 2008/0249384 | A1 | 10/2008 | Skyggebjerg et al. |
| 2008/0312859 | A1 | 12/2008 | Skyggebjerg et al. |
| 2009/0171226 | A1 | 7/2009 | Campbell et al. |
| 2010/0249549 | A1 | 9/2010 | Baker, Jr. et al. |
| 2010/0330598 | A1 | 12/2010 | Thukral et al. |
| 2011/0004081 | A1 | 1/2011 | Addison et al. |
| 2011/0028854 | A1 | 2/2011 | Addison et al. |
| 2011/0071406 | A1 | 3/2011 | Addison et al. |
| 2011/0205535 | A1 | 8/2011 | Soller et al. |
| 2011/0265795 | A1 | 11/2011 | Tagawa et al. |
| 2011/0270560 | A1 | 11/2011 | Wang et al. |
| 2012/0016179 | A1 | 1/2012 | Paradis et al. |
| 2013/0211214 | A1 | 8/2013 | Olsen |

FOREIGN PATENT DOCUMENTS

| | | |
|---|---|---|
| WO | WO-2002079758 | 10/2002 |
| WO | WO-2012084726 | 6/2012 |

* cited by examiner

METHODS AND SYSTEMS FOR DYNAMIC DISPLAY OF A TRACE OF A PHYSIOLOGICAL PARAMETER

CROSS REFERENCE TO RELATED APPLICATION

This application claims the benefit of U.S. Provisional Application No. 61/886,578, filed Oct. 3, 2013, which is hereby incorporated by reference herein in its entirety.

SUMMARY

The present disclosure relates to displaying physiological information with a physiological monitor, and more particularly, relates to dynamically displaying a trace of a physiological parameter with a pulse oximeter or other medical device.

Methods and systems are provided for displaying physiological information. In some embodiments, a system receives a physiological signal from a subject, for example, a photoplethysmograph (PPG) signal, and processes it to determine a physiological parameter of the subject, for example blood oxygen saturation. The system determines metrics for the received physiological signal and uses the metrics to determine display parameters. The system varies characteristics of the trace of the physiological parameter based on the display parameters.

In some embodiments, a system for displaying physiological information includes processing equipment configured for receiving a physiological signal from a subject and determining a physiological parameter of the subject based at least in part on the received physiological signal. The processing equipment is further configured for determining one or more metrics associated with the physiological signal and determining a width parameter based at least in part on the one or more metrics. The processing equipment is further configured for displaying the trace of the physiological parameter based at least in part on the width parameter.

In some embodiments, a method for displaying physiological information includes receiving a physiological signal from a subject and determining a physiological parameter of the subject based at least in part on the received physiological signal. The method includes determining one or more metrics associated with the physiological signal and determining a width parameter based at least in part on the one or more metrics. The method includes displaying the trace of the physiological parameter based at least in part on the width parameter.

In some embodiments, a system for displaying physiological information includes processing equipment configured for receiving a physiological signal from a subject and determining a physiological parameter of the subject based at least in part on the received physiological signal. The processing equipment is further configured for determining one or more confidence metrics associated with the physiological parameter and determining a width parameter based at least in part on the one or more confidence metrics. The processing equipment is further configured for continuously displaying the physiological parameter based at least in part on the width parameter.

In some embodiments, a method for displaying physiological information includes receiving a physiological signal from a subject and determining a physiological parameter of the subject based at least in part on the received physiological signal. The method includes determining one or more confidence metrics associated with the physiological parameter and determining a width parameter based at least in part on the one or more confidence metrics. The method includes continuously displaying the physiological parameter based at least in part on the width parameter.

In some embodiments, a system for displaying physiological information includes processing equipment configured for receiving a physiological signal from a subject and determining a physiological parameter of the subject based at least in part on the received physiological signal. The processing equipment is further configured for determining one or more metrics associated with the physiological parameter and determining a distance parameter based at least in part on the one or more metrics. The processing equipment is further configured for displaying a trace of the physiological parameter based at least in part on the distance parameter, where the trace comprises an upper bound and a lower bound, and a distance between the upper bound and lower bound is varied based on the distance parameter.

In some embodiments, a method for displaying physiological information includes receiving a physiological signal from a subject and determining a physiological parameter of the subject based at least in part on the received physiological signal. The method includes determining one or more metrics associated with the physiological parameter and determining a distance parameter based at least in part on the one or more metrics. The method includes displaying a trace of the physiological parameter based at least in part on the distance parameter, where the trace comprises an upper bound and a lower bound, and a distance between the upper bound and lower bound is varied based on the distance parameter.

BRIEF DESCRIPTION OF THE FIGURES

The above and other features of the present disclosure, its nature and various advantages will be more apparent upon consideration of the following detailed description, taken in conjunction with the accompanying drawings in which.

DETAILED DESCRIPTION OF THE FIGURES

Figure 1:
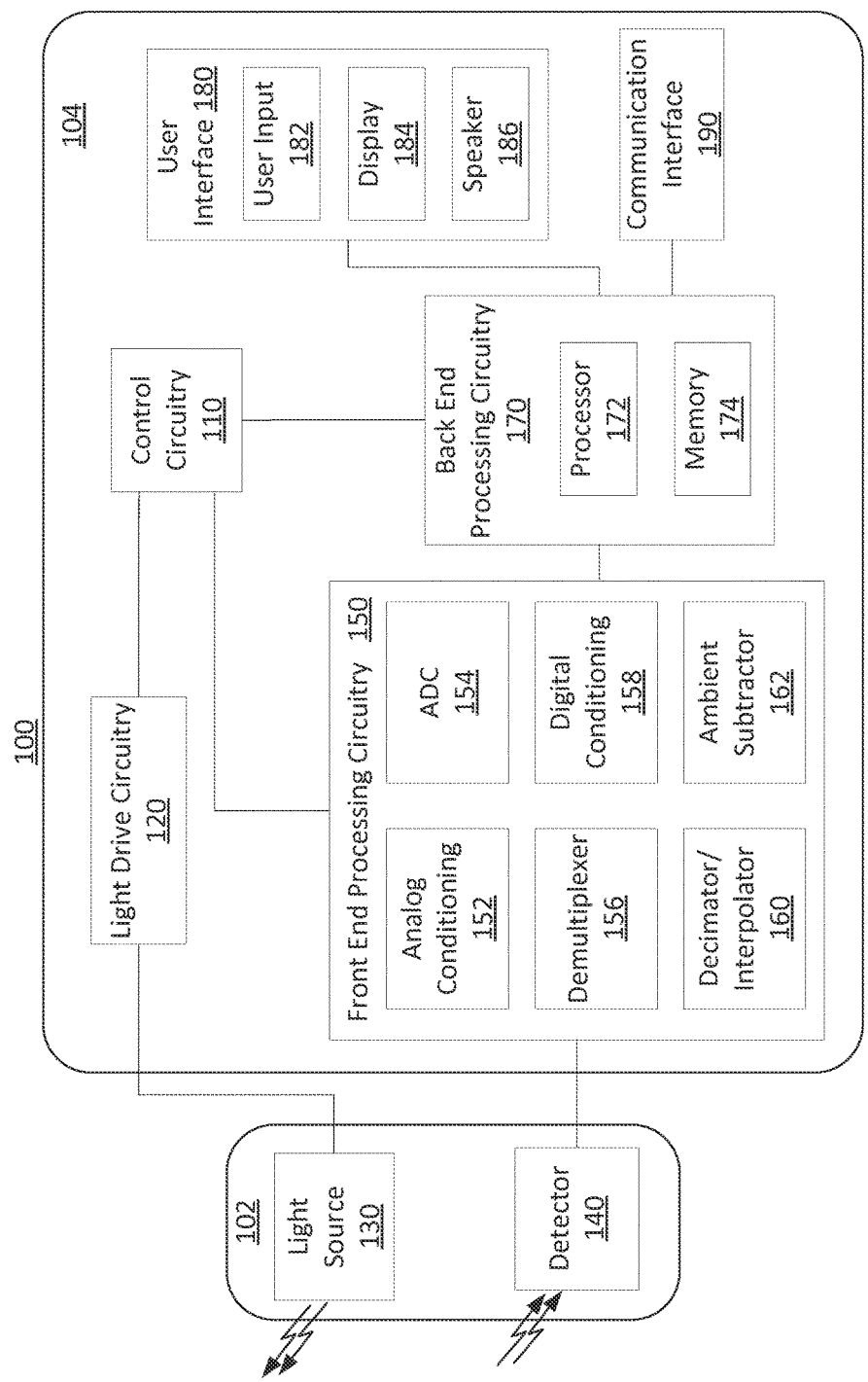
FIG. 1 is a block diagram of an illustrative physiological monitoring system in accordance with some embodiments of the present disclosure.

The present disclosure is directed towards displaying physiological information with a physiological monitor. A physiological parameter is computed from a received physiological signal. Metrics are determined for the received physiological signal or the determined physiological parameter. For example, a metric corresponding to a statistical measure of uncertainty of the physiological parameter values may be determined. One or more display parameters are determined based at least in part on the metrics. A trace of the computed physiological parameter for a subject is generated and displayed. The term trace, as used herein, refers to a graphical display object that is representative of physiological data. One or more characteristics of the displayed trace may be varied according to the display parameters. The variations in the one or more characteristics of the displayed trace may provide dynamic, graphical representations of, for example, the uncertainty of the computed values of the physiological parameter.

Measured data, including physiological data, is inherently uncertain, due to errors arising from physical processes in the subject being monitored and the methods and equipment used to obtain the physiological information. In determining a physiological parameter, significant uncertainties may be removed by applying a filtering or averaging algorithm to the received physiological signal before computing values of the physiological parameter. The uncertainty, however, may be an important indicator of signal quality and artifact. In some embodiments, the present disclosure varies the display of a trace of a physiological parameter according to a statistical measure of uncertainty and/or other metrics associated with the received physiological signal, so as to provide a real-time or historical representation of both the computed physiological parameter and the corresponding uncertainty in the parameter.

In some embodiments, the displayed trace of a physiological parameter may be varied based on one or more display parameters, which may be determined based at least in part on the one or more metrics associated with the physiological signal. A display parameter may correspond to a modifiable characteristic of the displayed trace. For example, the display parameters may include a width parameter that corresponds to a width associated with the displayed trace. In another example, the display parameters may include a distance parameter that corresponds to a distance between upper and lower bounds of the displayed trace. In some embodiments, additional or alternative characteristics of the displayed trace may be varied based on one or more display parameters, including color, translucency, line style, any other suitable display parameters, and any suitable combination thereof. The ability to vary the trace of the physiological parameter based on one or more display parameters allows for the trace to convey multiple types of information in a simple, uncluttered, and effective manner. For example, particular types of uncertainty, such as artifact caused by a particular source, can be emphasized in the graphical representation.

The foregoing techniques may be implemented in an oximeter. An oximeter is a medical device that may determine the oxygen saturation of an analyzed tissue. One common type of oximeter is a pulse oximeter, which may non-invasively measure the oxygen saturation of a patient's blood (as opposed to measuring oxygen saturation directly by analyzing a blood sample taken from the patient). Pulse oximeters may be included in patient monitoring systems that measure and display various blood flow characteristics including, but not limited to, the oxygen saturation of hemoglobin in arterial blood. Such patient monitoring systems may also measure and display additional physiological parameters, such as a patient's pulse rate, respiration rate, respiration effort, blood pressure, any other suitable physiological parameter, or any combination thereof. Exemplary embodiments of determining respiration rate are disclosed in Addison et al. U.S. Patent Publication No. 2011/0071406, published Mar. 24, 2011, which is hereby incorporated by reference herein in its entirety. Exemplary embodiments of determining respiration effort are disclosed in Addison et al. U.S. Patent Publication No. 2011/0004081, published Jan. 6, 2011, which is hereby incorporated by reference herein in its entirety. Exemplary embodiments of determining blood pressure are disclosed in Addison et al. U.S. Patent Publication No. 2011/0028854, published Feb. 3, 2011, which is hereby incorporated by reference herein in its entirety. Pulse oximetry may be implemented using a photoplethysmograph. Pulse oximeters and other photoplethysmograph devices may also be used to determine other physiological parameter and information as disclosed in: J. Allen, "Photoplethysmography and its application in clinical physiological measurement," *Physiol. Meas.*, vol. 28, pp. R1-R39, March 2007; W. B. Murray and P. A. Foster, "The peripheral pulse wave: information overlooked," *J. Clin. Monit.*, vol. 12, pp. 365-377, September 1996; and K. H. Shelley, "Photoplethysmography: beyond the calculation of arterial oxygen saturation and heart rate," *Anesth. Analg.*, vol. 105, pp. S31-S36, December 2007; all of which are incorporated by reference herein in their entireties.

An oximeter may include a light sensor that is placed at a site on a patient, typically a fingertip, toe, forehead or earlobe, or in the case of a neonate, across a foot or hand. The oximeter may use a light source to pass light through blood perfused tissue and photoelectrically sense the absorption of the light in the tissue. Additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, around or in front of the ear, and locations with strong pulsatile arterial flow. Suitable sensors for these locations may include sensors that detect reflected light.

The oximeter may measure the intensity of light that is received at the light sensor as a function of time. The oximeter may also include sensors at multiple locations. A signal representing light intensity versus time or a mathematical manipulation of this signal (e.g., a scaled version thereof, a log taken thereof, a scaled version of a log taken thereof, an inverted signal, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof.

The light intensity or the amount of light absorbed may then be used to calculate any of a number of physiological parameters, including an amount of a blood constituent (e.g., oxyhemoglobin) being measured as well as a pulse rate and when each individual pulse occurs.

In some embodiments, the photonic signal interacting with the tissue is of one or more wavelengths that are attenuated by the blood in an amount representative of the blood constituent concentration. Red and infrared (IR) wavelengths may be used because it has been observed that highly oxygenated blood will absorb relatively less red light and more IR light than blood with a lower oxygen saturation. By comparing the intensities of two wavelengths at different points in the pulse cycle, it is possible to estimate the blood oxygen saturation of hemoglobin in arterial blood.

The system may process data to determine physiological parameters using techniques well known in the art. For example, the system may determine blood oxygen saturation using two wavelengths of light and a ratio-of-ratios calculation. The system also may identify pulses and determine pulse amplitude, respiration, blood pressure, other suitable parameters, or any combination thereof, using any suitable calculation techniques. In some embodiments, the system may use information from external sources (e.g., tabulated data, secondary sensor devices) to determine physiological parameters.

The following description and accompanying FIGS. 1-11 provide additional details and features of some embodiments of the present disclosure.

FIG. 1 is a block diagram of an illustrative physiological monitoring system 100 in accordance with some embodiments of the present disclosure. System 100 may include a sensor 102 and a monitor 104 for generating and processing physiological signals of a subject. In some embodiments, sensor 102 and monitor 104 may be part of an oximeter.

Sensor 102 of physiological monitoring system 100 may include light source 130 and detector 140. Light source 130 may be configured to emit photonic signals having one or more wavelengths of light (e.g. red and IR) into a subject's tissue. For example, light source 130 may include a red light emitting light source and an IR light emitting light source, e.g. red and IR light emitting diodes (LEDs), for emitting light into the tissue of a subject to generate physiological signals. In one embodiment, the red wavelength may be between about 600 nm and about 700 nm, and the IR wavelength may be between about 800 nm and about 1000 nm. It will be understood that light source 130 may include any number of light sources with any suitable characteristics. In embodiments where an array of sensors is used in place of single sensor 102, each sensor may be configured to emit a single wavelength. For example, a first sensor may emit only a red light while a second may emit only an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 140 may be chosen to be specifically sensitive to the chosen targeted energy spectrum of light source 130.

In some embodiments, detector 140 may be configured to detect the intensity of light at the red and IR wavelengths. In some embodiments, an array of sensors may be used and each sensor in the array may be configured to detect an intensity of a single wavelength. In operation, light may enter detector 140 after passing through the subject's tissue. Detector 140 may convert the intensity of the received light into an electrical signal. The light intensity may be directly related to the absorbance and/or reflectance of light in the tissue. That is, when more light at a certain wavelength is absorbed or reflected, less light of that wavelength is received from the tissue by detector 140. After converting the received light to an electrical signal, detector 140 may send the detection signal to monitor 104, where the detection signal may be processed and physiological parameters may be determined (e.g., based on the absorption of the red and IR wavelengths in the subject's tissue). In some embodiments, the detection signal may be preprocessed by sensor 102 before being transmitted to monitor 104.

In the embodiment shown, monitor 104 includes control circuitry 110, light drive circuitry 120, front end processing circuitry 150, back end processing circuitry 170, user interface 180, and communication interface 190. Monitor 104 may be communicatively coupled to sensor 102.

Control circuitry 110 may be coupled to light drive circuitry 120, front end processing circuitry 150, and back end processing circuitry 170, and may be configured to control the operation of these components. In some embodiments, control circuitry 110 may be configured to provide timing control signals to coordinate their operation. For example, light drive circuitry 120 may generate one or more light drive signals, which may be used to turn on and off the light source 130, based on the timing control signals. The front end processing circuitry 150 may use the timing control signals to operate synchronously with light drive circuitry 120. For example, front end processing circuitry 150 may synchronize the operation of an analog-to-digital converter and a demultiplexer with the light drive signal based on the timing control signals. In addition, the back end processing circuitry 170 may use the timing control signals to coordinate its operation with front end processing circuitry 150.

Light drive circuitry 120, as discussed above, may be configured to generate a light drive signal that is provided to light source 130 of sensor 102. The light drive signal may, for example, control the intensity of light source 130 and the timing of when light source 130 is turned on and off. In some embodiments, light drive circuitry 130 provides one or more light drive signals to light source 130. Where light source 130 is configured to emit two or more wavelengths of light, the light drive signal may be configured to control the operation of each wavelength of light. The light drive signal may comprise a single signal or may comprise multiple signals (e.g., one signal for each wavelength of light).

In some embodiments, control circuitry 110 and light drive circuitry 120 may generate light drive parameters based on a metric. For example, back end processing 170 may receive information about received light signals, determine light drive parameters based on that information, and send corresponding information to control circuitry 110.

Figure 2A:
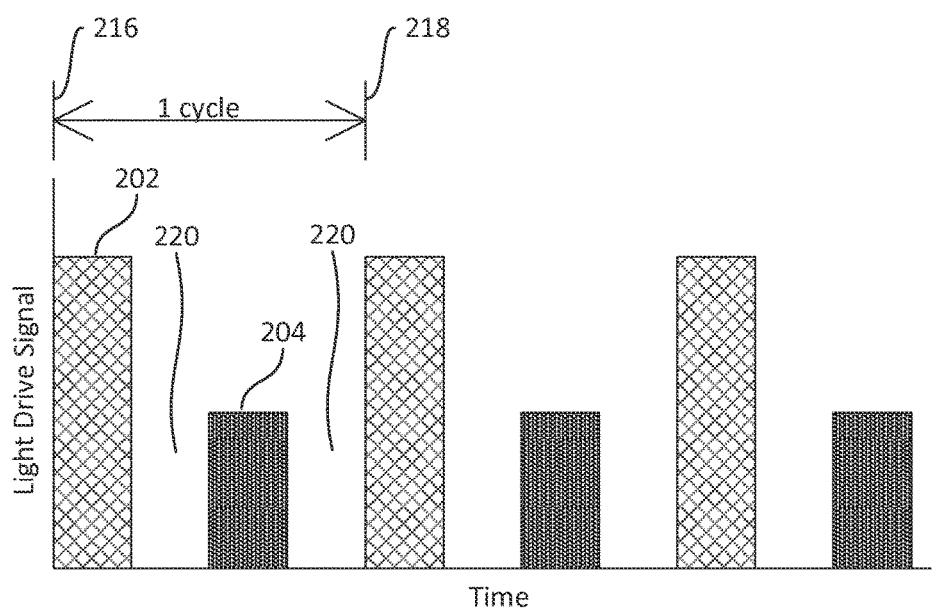
FIG. 2A shows an illustrative plot of a light drive signal in accordance with some embodiments of the present disclosure.

FIG. 2A shows an illustrative plot of a light drive signal including red light drive pulse 202 and IR light drive pulse 204 in accordance with some embodiments of the present disclosure. In the illustrated embodiment, light drive pulses 202 and 204 are shown as square waves. It will be understood that square waves are presented merely as an illustrative example, not by way of limitation, and that these pulses may include any other suitable signal, for example, shaped pulse waveforms, rather than a square waves. The shape of the pulses may be generated by a digital signal generator, digital filters, analog filters, any other suitable equipment, or any combination thereof. For example, light drive pulses 202 and 204 may be generated by light drive circuitry 120 under the control of control circuitry 110. As used herein, drive pulses may refer to the high and low states of a pulse, switching power or other components on and off, high and low output states, high and low values within a continuous modulation, other suitable relatively distinct states, or any combination thereof. The light drive signal may be provided to light source 130, including red light drive pulse 202 and IR light drive pulse 204 to drive red and IR light emitters, respectively, within light source 130.

Red light drive pulse 202 may have a higher amplitude than IR light drive 204 since red LEDs may be less efficient than IR LEDs at converting electrical energy into light energy. In some embodiments, the output levels may be equal, may be adjusted for nonlinearity of emitters, may be modulated in any other suitable technique, or any combination thereof. Additionally, red light may be absorbed and scattered more than IR light when passing through perfused tissue.

When the red and IR light sources are driven in this manner they emit pulses of light at their respective wavelengths into the tissue of a subject in order generate physiological signals that physiological monitoring system 100 may process to calculate physiological parameters. It will be understood that the light drive amplitudes of FIG. 2A are merely exemplary and that any suitable amplitudes or combination of amplitudes may be used, and may be based on the light sources, the subject tissue, the determined physiological parameter, modulation techniques, power sources, any other suitable criteria, or any combination thereof.

The light drive signal of FIG. 2A may also include "off" periods 220 between the red and IR light drive pulse. "Off" periods 220 are periods during which no drive current may be applied to light source 130. "Off" periods 220 may be provided, for example, to prevent overlap of the emitted light, since light source 130 may require time to turn completely on and completely off. The period from time 216 to time 218 may be referred to as a drive cycle, which includes four segments: a red light drive pulse 202, followed by an "off" period 220, followed by an IR light drive pulse 204, and followed by an "off" period 220. After time 218, the drive cycle may be repeated (e.g., as long as a light drive signal is provided to light source 130). It will be understood that the starting point of the drive cycle is merely illustrative and that the drive cycle can start at any location within FIG. 2A, provided the cycle spans two drive pulses and two "off" periods. Thus, each red light drive pulse 202 and each IR light drive pulse 204 may be understood to be surrounded by two "off" periods 220. "Off" periods may also be referred to as dark periods, in that the emitters are dark or returning to dark during that period. It will be understood that the particular square pulses illustrated in FIG. 2A are merely exemplary and that any suitable light drive scheme is possible. For example, light drive schemes may include shaped pulses, sinusoidal modulations, time division multiplexing other than as shown, frequency division multiplexing, phase division multiplexing, any other suitable light drive scheme, or any combination thereof.

Referring back to FIG. 1, front end processing circuitry 150 may receive a detection signal from detector 140 and provide one or more processed signals to back end processing circuitry 170. The term "detection signal," as used herein, may refer to any of the signals generated within front end processing circuitry 150 as it processes the output signal of detector 140. Front end processing circuitry 150 may perform various analog and digital processing of the detector signal. One suitable detector signal that may be received by front end processing circuitry 150 is shown in FIG. 2B.

Figure 2B:
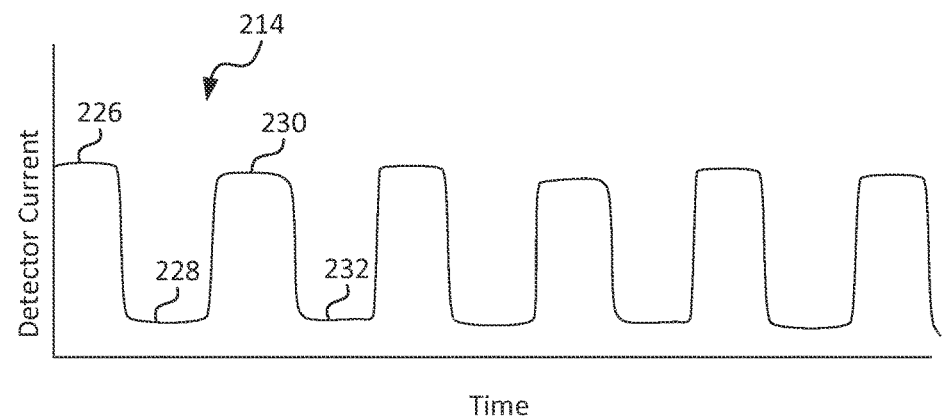
FIG. 2B shows an illustrative plot of a detector signal that may be generated by a sensor in accordance with some embodiments of the present disclosure.

FIG. 2B shows an illustrative plot of detector current waveform 214 that may be generated by a sensor in accordance with some embodiments of the present disclosure. The peaks of detector current waveform 214 may represent current signals provided by a detector, such as detector 140 of FIG. 1, when light is being emitted from a light source. The amplitude of detector current waveform 214 may be proportional to the light incident upon the detector. The peaks of detector current waveform 214 may be synchronous with drive pulses driving one or more emitters of a light source, such as light source 130 of FIG. 1. For example, detector current peak 226 may be generated in response to a light source being driven by red light drive pulse 202 of FIG. 2A, and peak 230 may be generated in response to a light source being driven by IR light drive pulse 204. Valley 228 of detector current waveform 214 may be synchronous with periods of time during which no light is being emitted by the light source, or the light source is returning to dark, such as "off" period 220. While no light is being emitted by a light source during the valleys, detector current waveform 214 may not fall all of the way to zero.

It will be understood that detector current waveform 214 may be an at least partially idealized representation of a detector signal, assuming perfect light signal generation, transmission, and detection. It will be understood that an actual detector current will include amplitude fluctuations, frequency deviations, droop, overshoot, undershoot, rise time deviations, fall time deviations, other deviations from the ideal, or any combination thereof. It will be understood that the system may shape the drive pulses shown in FIG. 2A in order to make the detector current as similar as possible to idealized detector current waveform 214.

Referring back to FIG. 1, front end processing circuitry 150, which may receive a detection signal, such as detector current waveform 214, may include analog conditioning 152, analog-to-digital converter (ADC) 154, demultiplexer 156, digital conditioning 158, decimator/interpolator 160, and ambient subtractor 162.

Analog conditioning 152 may perform any suitable analog conditioning of the detector signal. The conditioning performed may include any type of filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof.

The conditioned analog signal may be processed by analog-to-digital converter 154, which may convert the conditioned analog signal into a digital signal. Analog-to-digital converter 154 may operate under the control of control circuitry 110. Analog-to-digital converter 154 may use timing control signals from control circuitry 110 to determine when to sample the analog signal. Analog-to-digital converter 154 may be any suitable type of analog-to-digital converter of sufficient resolution to enable a physiological monitor to accurately determine physiological parameters.

Demultiplexer 156 may operate on the analog or digital form of the detector signal to separate out different components of the signal. For example, detector current waveform 214 of FIG. 2B includes a red component corresponding to peak 226, an IR component corresponding to peak 230, and at least one ambient component corresponding to valley 230. Demultiplexer 156 may operate on detector current waveform 214 of FIG. 2B to generate a red signal, an IR signal, a first ambient signal (e.g., corresponding to the ambient component corresponding to valley 230 that occurs immediately after the peak 226), and a second ambient signal (e.g., corresponding to the ambient component corresponding to valley 230 that occurs immediately after the IR component 230). Demultiplexer 156 may operate under the control of control circuitry 110. For example, demultiplexer 156 may use timing control signals from control circuitry 110 to identify and separate out the different components of the detector signal.

Digital conditioning 158 may perform any suitable digital conditioning of the detector signal. Digital conditioning 158 may include any type of digital filtering of the signal (e.g., low pass, high pass, band pass, notch, averaging, or any other suitable filtering), amplifying, performing an operation on the signal, performing any other suitable digital conditioning, or any combination thereof.

Decimator/interpolator 160 may decrease the number of samples in the digital detector signal. For example, decimator/interpolator 160 may decrease the number of samples by removing samples from the detector signal or replacing samples with a smaller number of samples. The decimation or interpolation operation may include or be followed by filtering to smooth the output signal.

Ambient subtractor 162 may operate on the digital signal. In some embodiments, ambient subtractor 162 may remove dark or ambient contributions to the received signal.

The components of front end processing circuitry 150 are merely illustrative and any suitable components and combinations of components may be used to perform the front end processing operations.

The front end processing circuitry 150 may be configured to take advantage of the full dynamic range of analog-to-digital converter 154. This may be achieved by applying gain to the detection signal by analog conditioning 152 to map the expected range of the detection signal to the full or close to full output range of analog-to-digital converter 154. The output value of analog-to-digital converter 154, as a function of the total analog gain applied to the detection signal, may be given as:

ADC Value=Total Analog Gain×[Ambient Light+ LED Light]

Ideally, when ambient light is zero and when the light source is off, the analog-to-digital converter 154 will read just above the minimum input value. When the light source is on, the total analog gain may be set such that the output of analog-to-digital converter 154 may read close to the full scale of analog-to-digital converter 154 without saturating. This may allow the full dynamic range of analog-to-digital converter 154 to be used for representing the detection signal, thereby increasing the resolution of the converted signal. In some embodiments, the total analog gain may be reduced by a small amount so that small changes in the light level incident on the detector do not cause saturation of analog-to-digital converter 154.

However, if the contribution of ambient light is large relative to the contribution of light from a light source, the total analog gain applied to the detection current may need to be reduced to avoid saturating analog-to-digital converter 154. When the analog gain is reduced, the portion of the signal corresponding to the light source may map to a smaller number of analog-to-digital conversion bits. Thus, more ambient light noise in the input of analog-to-digital converter 154 may result in fewer bits of resolution for the portion of the signal from the light source. This may have a detrimental effect on the signal-to-noise ratio of the detection signal. Accordingly, passive or active filtering or signal modification techniques may be employed to reduce the effect of ambient light on the detection signal that is applied to analog-to-digital converter 154, and thereby reduce the contribution of the noise component to the converted digital signal.

Back end processing circuitry 170 may include processor 172 and memory 174. Processor 172 may be adapted to execute software, which may include an operating system and one or more applications, as part of performing the functions described herein. Processor 172 may receive and further process physiological signals received from front end processing circuitry 150. For example, processor 172 may determine one or more physiological parameters based on the received physiological signals. Processor 172 may include an assembly of analog or digital electronic components. Processor 172 may calculate physiological information. For example, processor 172 may compute one or more of blood oxygen saturation (e.g., arterial, venous, or both), pulse rate, respiration rate, respiration effort, blood pressure, hemoglobin concentration (e.g., oxygenated, deoxygenated, and/or total), any other suitable physiological parameters, or any combination thereof. Processor 172 may perform any suitable signal processing of a signal, such as any suitable band-pass filtering, adaptive filtering, closed-loop filtering, any other suitable filtering, and/or any combination thereof. Processor 172 may also receive input signals from additional sources not shown. For example, processor 172 may receive an input signal containing information about treatments provided to the subject from user interface 180. Additional input signals may be used by processor 172 in any of the calculations or operations it performs in accordance with back end processing circuitry 170 or monitor 104.

Memory 174 may include any suitable computer-readable media capable of storing information that can be interpreted by processor 172. In some embodiments, memory 174 may store calculated values, such as pulse rate, blood pressure, blood oxygen saturation, fiducial point locations or characteristics, initialization parameters, any other calculated values, or any combination thereof, in a memory device for later retrieval. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system. Back end processing circuitry 170 may be communicatively coupled with user interface 180 and communication interface 190.

User interface 180 may include user input 182, display 184, and speaker 186. User interface 180 may include, for example, any suitable device such as one or more medical devices (e.g., a medical monitor that displays various physiological parameters, a medical alarm, or any other suitable medical device that either displays physiological parameters or uses the output of back end processing 170 as an input), one or more display devices (e.g., monitor, personal digital assistant (PDA), mobile phone, tablet computer, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

User input 182 may include any type of user input device such as a keyboard, a mouse, a touch screen, buttons, switches, a microphone, a joy stick, a touch pad, or any other suitable input device. The inputs received by user input 182 can include information about the subject, such as age, weight, height, diagnosis, medications, treatments, and so forth.

In an embodiment, the subject may be a medical patient and display 184 may exhibit a list of values which may generally apply to the patient, such as, for example, age ranges or medication families, which the user may select using user input 182. Additionally, display 184 may display, for example, an estimate of a subject's blood oxygen saturation generated by monitor 104 (referred to as an "SpO$_2$" measurement), pulse rate information, respiration rate information, blood pressure, any other parameters, and any combination thereof. Display 184 may include any type of display such as a cathode ray tube display, a flat panel display such a liquid crystal display or plasma display, or any other suitable display device. Speaker 186 within user interface 180 may provide an audible sound that may be used in various embodiments, such as for example, sounding an audible alarm in the event that a patient's physiological parameters are not within a predefined normal range.

Communication interface 190 may enable monitor 104 to exchange information with external devices. Communications interface 190 may include any suitable hardware, software, or both, which may allow monitor 104 to communicate with electronic circuitry, a device, a network, a server or other workstations, a display, or any combination thereof. Communications interface 190 may include one or more receivers, transmitters, transceivers, antennas, plug-in connectors, ports, communications buses, communications protocols, device identification protocols, any other suitable hardware or software, or any combination thereof. Communications interface 190 may be configured to allow wired communication (e.g., using USB, RS-232, Ethernet, or other standards), wireless communication (e.g., using WiFi, IR, WiMax, BLUETOOTH, USB, or other standards), or both. For example, communications interface 190 may be configured using a universal serial bus (USB) protocol (e.g., USB 2.0, USB 3.0), and may be configured to couple to other devices (e.g., remote memory devices storing templates) using a four-pin USB standard Type-A connector (e.g., plug and/or socket) and cable. In some embodiments, communications interface 190 may include an internal bus such as, for example, one or more slots for insertion of expansion cards.

It will be understood that the components of physiological monitoring system 100 that are shown and described as separate components are shown and described as such for illustrative purposes only. In some embodiments the functionality of some of the components may be combined in a single component. For example, the functionality of front end processing circuitry 150 and back end processing circuitry 170 may be combined in a single processor system. Additionally, in some embodiments the functionality of some of the components of monitor 104 shown and described herein may be divided over multiple components. For example, some or all of the functionality of control circuitry 110 may be performed in front end processing circuitry 150, in back end processing circuitry 170, or both. In other embodiments, the functionality of one or more of the components may be performed in a different order or may not be required. In an embodiment, all of the components of physiological monitoring system 100 can be realized in processor circuitry.

Figure 3:
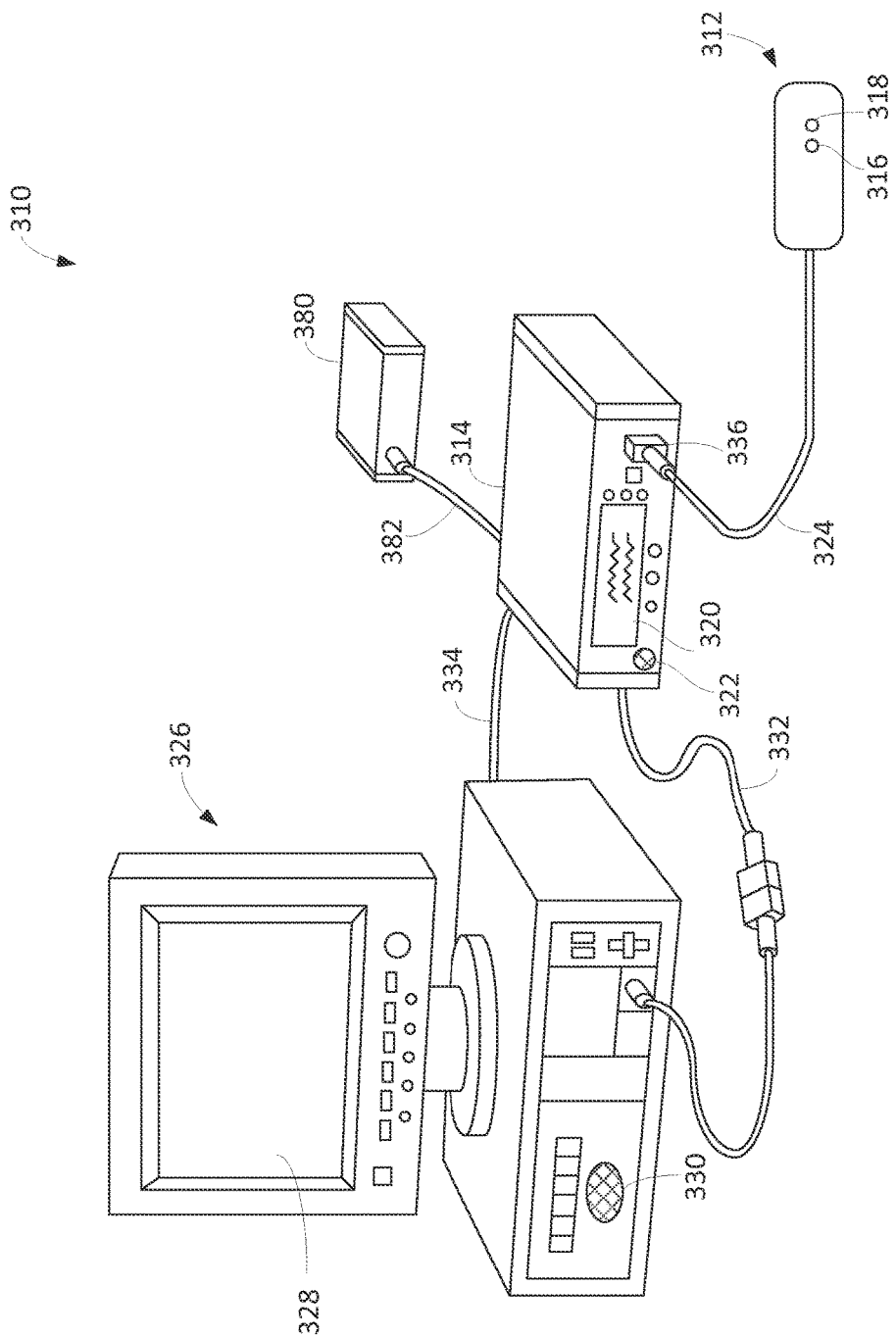
FIG. 3 is a perspective view of an illustrative physiological monitoring system in accordance with some embodiments of the present disclosure.

FIG. 3 is a perspective view of an illustrative physiological monitoring system 310 in accordance with some embodiments of the present disclosure. In some embodiments, one or more components of physiological monitoring system 310 may include one or more components of physiological monitoring system 100 of FIG. 1. Physiological monitoring system 310 may include sensor unit 312 and monitor 314. In some embodiments, sensor unit 312 may be part of an oximeter. Sensor unit 312 may include one or more light source 316 for emitting light at one or more wavelengths into a subject's tissue. One or more detector 318 may also be provided in sensor unit 312 for detecting the light that is reflected by or has traveled through the subject's tissue. Any suitable configuration of light source 316 and detector 318 may be used. In an embodiment, sensor unit 312 may include multiple light sources and detectors, which may be spaced apart. Physiological monitoring system 310 may also include one or more additional sensor units (not shown) that may, for example, take the form of any of the embodiments described herein with reference to sensor unit 312. An additional sensor unit may be the same type of sensor unit as sensor unit 312, or a different sensor unit type than sensor unit 312 (e.g., a photoacoustic sensor). Multiple sensor units may be capable of being positioned at two different locations on a subject's body.

In some embodiments, sensor unit 312 may be connected to monitor 314 as shown. Sensor unit 312 may be powered by an internal power source, e.g., a battery (not shown). Sensor unit 312 may draw power from monitor 314. In another embodiment, the sensor may be wirelessly connected (not shown) to monitor 314. Monitor 314 may be configured to calculate physiological parameters based at least in part on data relating to light emission and acoustic detection received from one or more sensor units such as sensor unit 312. For example, monitor 314 may be configured to determine pulse rate, respiration rate, respiration effort, blood pressure, blood oxygen saturation (e.g., arterial, venous, or both), hemoglobin concentration (e.g., oxygenated, deoxygenated, and/or total), any other suitable physiological parameters, or any combination thereof. In some embodiments, calculations may be performed on the sensor units or an intermediate device and the result of the calculations may be passed to monitor 314. Further, monitor 314 may include display 320 configured to display the physiological parameters or other information about the system. In the embodiment shown, monitor 314 may also include a speaker 322 to provide an audible sound that may be used in various other embodiments, such as for example, sounding an audible alarm in the event that a subject's physiological parameters are not within a predefined normal range. In some embodiments, physiological monitoring system 310 may include a stand-alone monitor in communication with the monitor 314 via a cable or a wireless network link. In some embodiments, monitor 314 may be implemented as display 184 of FIG. 1.

In some embodiments, sensor unit 312 may be communicatively coupled to monitor 314 via a cable 324 at port 336. Cable 324 may include electronic conductors (e.g., wires for transmitting electronic signals from detector 318), optical fibers (e.g., multi-mode or single-mode fibers for transmitting emitted light from light source 316), any other suitable components, any suitable insulation or sheathing, or any combination thereof. In some embodiments, a wireless transmission device (not shown) or the like may be used instead of or in addition to cable 324. Monitor 314 may include a sensor interface configured to receive physiological signals from sensor unit 312, provide signals and power to sensor unit 312, or otherwise communicate with sensor unit 312. The sensor interface may include any suitable hardware, software, or both, which may be allow communication between monitor 314 and sensor unit 312.

In some embodiments, physiological monitoring system 310 may include calibration device 380. Calibration device 380, which may be powered by monitor 314, a battery, or by a conventional power source such as a wall outlet, may include any suitable calibration device. Calibration device 380 may be communicatively coupled to monitor 314 via communicative coupling 382, and/or may communicate wirelessly (not shown). In some embodiments, calibration device 380 is completely integrated within monitor 314. In some embodiments, calibration device 380 may include a manual input device (not shown) used by an operator to manually input reference signal measurements obtained from some other source (e.g., an external invasive or non-invasive physiological measurement system).

In the illustrated embodiment, physiological monitoring system 310 includes a multi-parameter physiological monitor 326. The monitor 326 may include a cathode ray tube display, a flat panel display (as shown) such as a liquid crystal display (LCD) or a plasma display, or may include any other type of monitor now known or later developed. Multi-parameter physiological monitor 326 may be configured to calculate physiological parameters and to provide a display 328 for information from monitor 314 and from other medical monitoring devices or systems (not shown). For example, multi-parameter physiological monitor 326 may be configured to display an estimate of a subject's blood oxygen saturation and hemoglobin concentration generated by monitor 314. Multi-parameter physiological monitor 326 may include a speaker 330.

Monitor 314 may be communicatively coupled to multi-parameter physiological monitor 326 via a cable 332 or 334 that is coupled to a sensor input port or a digital communications port, respectively and/or may communicate wirelessly (not shown). In addition, monitor 314 and/or multi-parameter physiological monitor 326 may be coupled to a network to enable the sharing of information with servers or other workstations (not shown). Monitor 314 may be powered by a battery (not shown) or by a conventional power source such as a wall outlet.

In some embodiments, any of the processing components and/or circuits, or portions thereof, of FIGS. 1 and 3, including sensors 102 and 312 and monitors 104, 314, and 326 may be referred to collectively as processing equipment. For example, processing equipment may be configured to amplify, filter, sample and digitize an input signal from sensor 102 or 312 (e.g., using an analog-to-digital converter), calculate physiological information and metrics from the digitized signal, and display a trace of the physiological information. In some embodiments, all or some of the components of the processing equipment may be referred to as a processing module.

Figure 4:
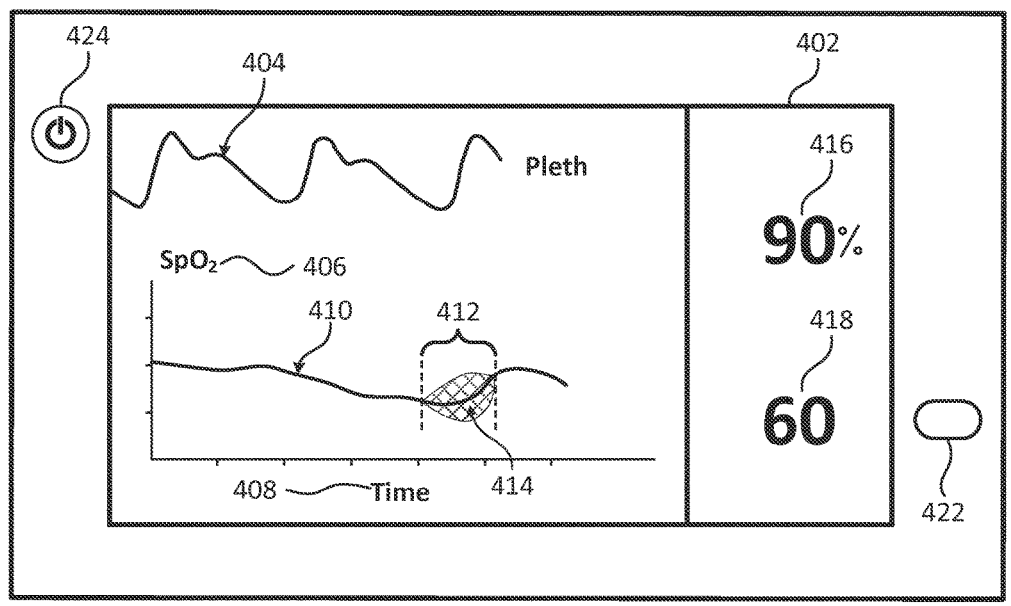
FIG. 4 shows an illustrative front panel of a physiological monitor in accordance with some embodiments of the present disclosure.

As discussed above, the processing equipment may receive a physiological signal from a patient. In some embodiments, the received physiological signal is a physiological light signal, such as a PPG signal. The physiological signal may be displayed on a front panel of the processing equipment. FIG. 4 shows an illustrative front panel 400 of a physiological monitor in accordance with some embodiments of the present disclosure. Front panel 400 may include, for example, display screen 402, button 422, and power button 424. In some embodiments, front panel 400 may correspond to the front panel of multi-parameter physiological monitor 326 or monitor 314 of FIG. 3 or monitor 104 of FIG. 1. More generally, front panel 400 may correspond to the front panel of any suitable processing equipment. In some embodiments, display screen 402 may correspond to display 184 of FIG. 1, display 328 of multi-parameter physiological monitor 326 or display 320 of monitor 314 of FIG. 3, or any other suitable display for depicting physiological information. In some embodiments, button 422 may include one or more buttons and may be configured to permit user input for various characteristics of the display shown on display screen 402. For example, button 422 may include functionality that permits a user to toggle between the display of different physiological parameters or units thereof or to input physiological data about a subject being monitored, to input threshold data, or any other functionality for affecting the presentation of data on the display screen 402 in accordance with some embodiments of the present disclosure. In some embodiments, power button 424 may act as a switch for turning the power to the physiological monitor or display screen 402 on and off. It will be understood that button 422 and power button 424 are presented merely for illustrative purposes and that front panel 400 may include any suitable buttons, controls, and combinations thereof.

In the embodiment shown, the processing equipment may display a received physiological signal on display screen 402 of FIG. 4 as plethysmograph (pleth) signal 404. For purposes of brevity and clarity, and not by way of limitation, the present disclosure describes and depicts the received physiological signal as being a PPG signal. It will be understood that the received physiological signal and the depicted signal in FIG. 4 are not limited to a PPG signal and may correspond to a biopotential signal, pressure signal, impedance signal, temperature signal, acoustic signal, any other suitable physiological signal, or any combination thereof.

In some embodiments, the processing equipment determines a physiological parameter based at least in part on the received physiological signal. In some embodiments, the processing equipment determines more than one physiological parameter based at least in part on the received physiological signal. The physiological parameters may include, for example, one or more of blood oxygen saturation (e.g., arterial, venous, or both), pulse rate, respiration rate, respiration effort, blood pressure, hemoglobin concentration (e.g., oxygenated, deoxygenated, and/or total), any other suitable physiological parameters, or any combination thereof. The processing equipment may display the computed physiological parameters on a display screen. In an example, the processing equipment may compute and display oxygen saturation 416 and pulse rate 418 on display screen 402 of FIG. 4. As illustrated, the current oxygen saturation is 90% and the current heart rate is 60 beats per minute. The determined physiological parameters may be displayed using an alphanumeric representation, graphical representation, any other suitable representation, or any combination thereof.

In some embodiments, the processing equipment may generate a trace of one or more physiological parameters.

The processing equipment may display a graphical representation of the trace over time. In some embodiments, the processing equipment may vary one or more characteristics of the trace based at least in part on one or more display parameters. Display parameters may include, for example, a width parameter, a color parameter, a translucence parameter, a style parameter, a distance parameter, any other suitable parameter for varying the display of a trace, or any combination thereof. The processing equipment may determine the one or more display parameters based at least in part on one or more metrics associated with the physiological signal. In some embodiments, the processing equipment may determine one or more metrics associated with the received physiological signal. In some embodiments, the one or more metrics may include metrics associated with a physiological parameter that is determined based at least in part on the physiological signal. Metrics may include, for example, any suitable measure or combination of measures for quantifying uncertainty, confidence, quality, data integrity, signal-to-noise ratio, accuracy, reliability, artifact, or interference from nearby equipment, ambient light, or otherwise, associated with the received physiological signal or the determined physiological parameter. In some embodiments, the one or more metrics may be confidence metrics. In some embodiments, the one or more metrics may form a confidence assessment associated with the physiological signal or physiological parameter. The determination of metrics is discussed in further detail below with reference to FIG. 10.

An exemplary graphical representation of a trace is shown on display screen 402 of FIG. 4 as trace 410. Trace 410 is depicted on a plot having a vertical axis 406 corresponding to oxygen saturation (SpO$_2$) and a horizontal axis 408 corresponding to time. Trace 410 shows the oxygen saturation of a patient over time. In some embodiments, the processing equipment varies one or more characteristics of trace 410 over time based at least in part on one or more respective display parameters. Each display parameter may correspond to a modifiable characteristic of the displayed trace.

Display screen 402 shows trace 410 with varied portion 412, in which one or more characteristics of trace 410 vary over time. In the embodiment shown, the processing equipment may vary the width of trace 410 along the length of varied portion 412 in response to a width parameter. In some embodiments, the processing equipment may vary one or more additional or alternative characteristics of trace 410 in response to respective additional or alternative display parameters. In the embodiment shown, the processing equipment may also vary at least one color 414 of trace 410 based on a color parameter, shown as a checkered pattern in varied portion 412. Characteristics of the displayed trace may include width, color, shading, pattern, solid or dashed style, luminosity, translucence, any other suitable characteristic of the displayed trace, or any combination thereof. In some embodiments, the processing equipment may vary a characteristic of the displayed trace based at least in part on a display parameter by generating an error flag, any other suitable marker, or any combination thereof. In some embodiments, the processing equipment dynamically updates the display parameters and dynamically varies corresponding characteristics of the displayed trace, presented in real-time or from historical data. For example, the processing equipment may dynamically vary the width associated with the displayed trace. In another example, the processing equipment may dynamically vary characteristics of a trace displayed on a scrolling display, so that the appearance of the trace may change over time as it is presented on the scrolling display. It will be understood that the scrolling display is merely exemplary and that any other suitable technique for displaying a trace or physiological parameter may be used, including, for example, any progressing display, dynamically updating display, continuous display, any other suitable, non-static display, and any combination thereof. Exemplary plots of traces including varied portions with one or more characteristics that are varied based at least in part on corresponding display parameters are shown in FIGS. 5-8.

FIGS. 5-8 show illustrative plots of traces of a physiological parameter in accordance with some embodiments of the present disclosure. It will be understood that the particular plots shown, and the signals of those plots, are merely exemplary. In some embodiments, a trace of a physiological parameter corresponds to the values of a physiological parameter over time. For purposes of brevity and clarity, and not by way of limitation, FIGS. 5-8 depict traces corresponding to oxygen saturation. It will be understood that the physiological parameter is not limited to oxygen saturation and may correspond to any suitable physiological parameter.

Figure 5:
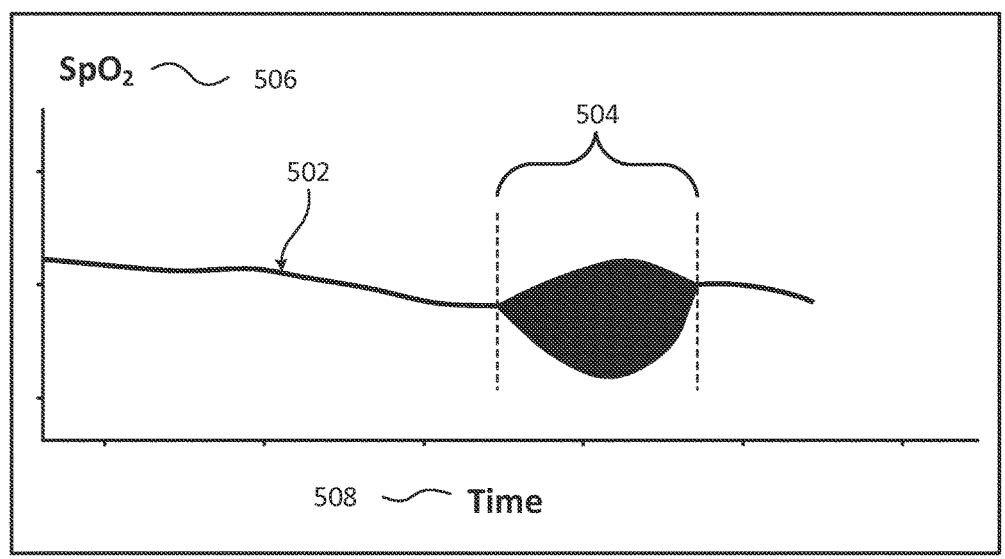
FIG. 5 shows an illustrative plot of a trace of a physiological parameter in accordance with some embodiments of the present disclosure.

FIG. 5 shows an illustrative plot 500 of trace 502 of a physiological parameter in accordance with some embodiments of the present disclosure. Vertical axis 506 of plot 500 corresponds to oxygen saturation and horizontal axis 508 corresponds to time. Trace 502 is depicted with varied portion 504 of varying width along its length.

In some embodiments, a width associated with a trace of a physiological parameter is varied based at least in part on a width parameter. In some embodiments, a physiological parameter is continuously displayed based at least in part on a width parameter. In the embodiment shown, trace 502 of plot 500 is shown with varied portion 504. Varied portion 504 illustrates a width associated with trace 502, which is varied along the length of trace 502 based at least in part on a width parameter. In some embodiments, a width parameter may correspond to a measure of width associated with trace 502. For example, the width associated with trace 502 may be modified dynamically based at least in part on a measure of width associated with trace 502. In some embodiments, the width parameters may be in units of the physiological parameter to which the trace corresponds, for example oxygen saturation. In some embodiments, a width parameter may depend on a range of physiologically acceptable values of the physiological parameter to which a trace corresponds. For example, trace 502 of plot 500 corresponds to oxygen saturation, and the operating range for oxygen saturation is 0%-100%, so varying a width associated with trace 502 may be based on a width parameter that is bound by a minimum value or a maximum value in this range. Thus, the varied width of varied portion 504 of trace 502 may not extend above or below the respective maximum or minimum possible values of oxygen saturation. In some embodiments the varied width may not extend above or below the range depicted on vertical axis 506 or any other suitable maximum or minimum values. In some embodiments, the width parameter may be adjusted according to the condition or circumstances of a subject. For example, the acceptable range for a physiological parameter may vary according to the condition or circumstances of the subject being monitored, and the width parameter may be determined so as to take into account the acceptable range for a physiological parameter specific to the subject being monitored.

In some embodiments, a width associated with a trace may be centered at the value of the physiological parameter to which the trace corresponds. In some embodiments, a width associated with a trace may be varied symmetrically, so that it increases or decreases by the same amount in the positive and negative directions relative to the vertical axis. In some embodiments, a width associated with a trace may be varied asymmetrically, so that it increases or decreases by differing amounts in the positive and negative directions relative to the vertical axis. For example, an acceptable range for oxygen saturation in healthy adults may be 91%-100%. The width associated with a trace may be centered at the computed value of the oxygen saturation, for example, 97%, and a statistical measure of uncertainty metric may indicate a range spanning 5% above and below the 97% value. The width parameter, however, may be determined so as to increase the width by 5% in the negative direction and by only 3% in the positive direction, as 100% is a physiological limit on oxygen saturation. Consequently, in the above example, the width associated with the trace is varied asymmetrically. In the embodiment shown, plot 500 shows trace 502 with varied portion 504 of varying width, where the width is depicted as being varied symmetrically at varied portion 504 by expanding an equal amount in the negative direction as in the positive direction, with respect to vertical axis 506.

Figure 6:
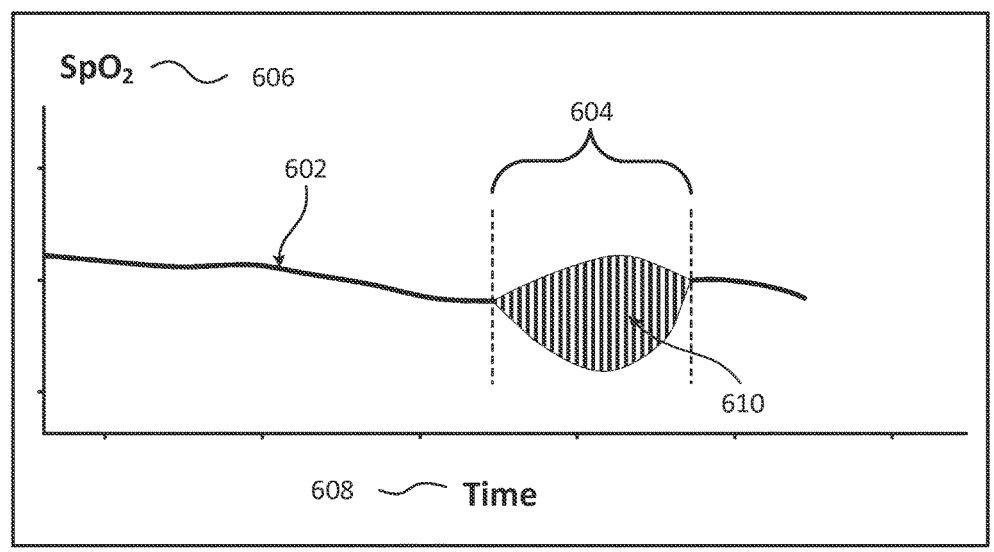
FIG. 6 shows an illustrative plot of a trace of a physiological parameter in accordance with some embodiments of the present disclosure.

FIG. 6 shows an illustrative plot 600 of trace 602 of a physiological parameter in accordance with some embodiments of the present disclosure. Vertical axis 606 of plot 600 corresponds to oxygen saturation and horizontal axis 608 corresponds to time. Trace 602 is depicted with varied portion 604 of varying width along its length. For clarity, varied portion 604 of trace 602 is shown with a varied width that corresponds to the varied width of varied portion 504 of trace 502, shown in FIG. 5. Varied portion 604 of trace 602 is also shown with varying color 610 along its length. The variation in color 610 of varied portion 604 is shown as a pattern of vertical stripes.

In some embodiments, a color associated with a trace of a physiological parameter is varied based at least in part on a color parameter. In the embodiment shown, trace 602 of plot 600 is shown with varied portion 604. Varied portion 604 illustrates color 610, which is varied along the length of trace 602 based at least in part on a color parameter. In some embodiments, the trace may include multiple colors that may be varied. In an example, the color of trace 602 may be varied such that varied portion 604 is partially green and partially blue. Varying a color may include, for example, varying a pattern, shading, hue, saturation, luminosity, any other suitable coloration technique, and any combination thereof.

In some embodiments, a color parameter may correspond to a particular metric or a value of a metric associated with the received physiological signal. Thus, in some embodiments, a variation in a color associated with a trace based at least in part on a color parameter may correspond to a metric or a value of a metric. In some embodiments, a value of a metric may be an indication of the severity of the metric, and the saturation of a color associated with a trace may be varied to correspond to the severity of the metric. For example, a lower-valued metric may be represented by a less saturated color, whereas a higher-valued metric may be represented by a more saturated color in the display of a trace of a physiological parameter. Thus, in the embodiment shown in plot 600, the saturation of color 610 of varied portion 604 of trace 602 may provide a visual indication of the severity of a metric associated with the received physiological signal.

In some embodiments, a metric associated with the received physiological signal may be indicative of an artifact event. Thus, in some embodiments, a variation in one or more colors associated with a trace based at least in part on a color parameter may provide a visual representation of an artifact event. Artifact events may include noise artifact, patient movement artifact, probe-off artifact, and other suitable non-physiological or undesired physiological signal components. For example, a red coloration of varied portion 604 of trace 602 may indicate a patient movement artifact, whereas a purple coloration of varied portion 604 of trace 602 may indicate probe-off artifact. In some embodiments, a combination of one or more metrics may provide an indication of an artifact event. In some embodiments, one or more metric thresholds on one or more respective metrics may be either predetermined or set by a user, and an artifact event may be identified based on a comparison of one or more determined metric values to the one or more respective metric thresholds. In some embodiments one or more metrics include a physiological range metric, which may be a measure of deviation of a determined value of a physiological parameter from a range of physiologically acceptable values. In an example, values may be determined for a signal quality metric and a physiological range metric, these determined metric values may be compared with respective metric thresholds, and if both exceed the respective metric threshold, a probe-off artifact event may be identified. A color parameter may be based at least in part on this identification of a probe-off artifact event, and a trace of a physiological parameter may be varied in response to the color parameter to provide a visual indication of a probe-off artifact event. It will be understood that the display of a trace may be varied based on any of the display parameters described herein to indicate an artifact event in accordance with some embodiments of the present disclosure and that the color parameter is presented merely as a non-limiting example. For example, the width parameter may be indicative of artifact associated with the physiological signal, so that the width of a displayed trace may be varied based on the width parameter to indicate an artifact event.

Figure 7:
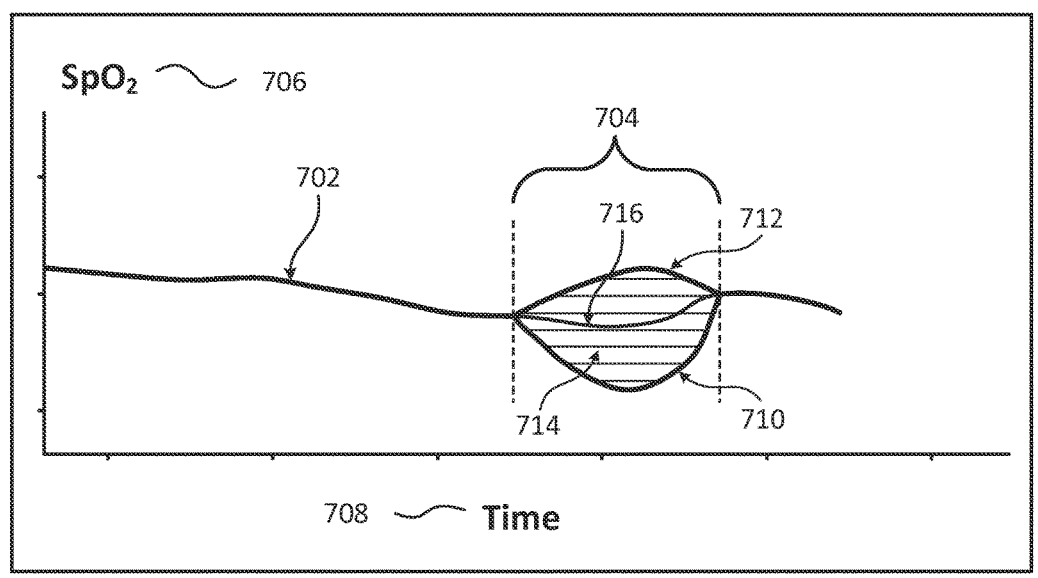
FIG. 7 shows an illustrative plot of a trace of a physiological parameter in accordance with some embodiments of the present disclosure.

FIG. 7 shows an illustrative plot 700 of trace 702 of a physiological parameter in accordance with some embodiments of the present disclosure. Vertical axis 706 of plot 700 corresponds to oxygen saturation and horizontal axis 708 corresponds to time. Trace 702 is depicted with varied portion 704 of varying width along its length. For clarity, varied portion 704 of trace 702 is shown with a varied width that corresponds to the varied width of varied portion 504 of trace 502, shown in FIG. 5, and of varied portion 604 of trace 602, shown in FIG. 6. Trace 702 is depicted as including upper bound 712, lower bound 710, and line 716. Line 716 may represent the determined values of a physiological parameter over time. Upper bound 712 and lower bound 710 define the varied width of varied portion 704 of trace 702, such that the upper and lower bounds form a perimeter of varied portion 704. Varied portion 704 of trace 702 is also shown with varying translucence 714 along its length. The variation in translucence 714 of varied portion 704 is shown in as a pattern of horizontal stripes.

In some embodiments, a translucence associated with a trace of a physiological parameter is varied based at least in part on a translucence parameter. In the embodiment shown, trace 702 of plot 700 is shown with varied portion 704. Varied portion 704 illustrates translucence 714, which is varied along the length of trace 702 based at least in part on a translucence parameter. In some embodiments, more than one translucence of displayed trace 702 may be varied. Varying a translucence may include, for example, varying a transparency, opacity, sharpness, any other suitable indicator of translucence, or any combination thereof.

In some embodiments, a translucence parameter may correspond to a particular metric or a value of a metric associated with the received physiological signal. Thus, in some embodiments, a variation in a translucence associated with a trace based at least in part on a translucence parameter may correspond to a metric or a value of a metric. In some embodiments, a value of a metric may be an indication of the severity of the metric. For example, a lower-valued metric may be represented by a less translucent variation, whereas a higher-valued metric may be represented by a more translucent variation. Thus, in the embodiment shown in plot 700, the translucence 714 of varied portion 704 of trace 702 may provide a visual indication of the severity of a metric associated with the received physiological signal.

In some embodiments, as shown in plot 700, line 716 may be displayed concurrently with upper bound 712 and lower bound 710. In some embodiments, the variation in translucence 714 of varied portion 704 determines whether or not line 716 is visible. For example, for a signal quality metric of a sufficiently low value, varying the translucence 714 may decrease the translucence 714 of varied portion 704 a sufficient amount so that line 716 is occluded from view. In the embodiment shown in plot 700, the variation in translucence 714 is such that line 716 is visible in varied portion 704 of trace 702. In some embodiments, a translucence threshold may be either predetermined or set by a user, such that whether or not line 716 is visible depends on whether a determined metric value falls above or below the translucence threshold.

In some embodiments, a width associated with a trace of a physiological parameter is varied based at least in part on a width parameter. In the embodiment shown, varied portion 704 of trace 702 is shown with varying width along its length, and the varying width is the vertical distance between upper bound 712 and lower bound 710. In some embodiments, the width of trace 702 may be varied by modifying at least one of the upper bound 712 and lower bound 710. For example, at least one of the upper bound 712 and lower bound 710 may be modified so that the width of varied portion 704 of trace 702 is varied asymmetrically about line 716. In the illustrated embodiment, upper bound 712 and lower bound 710 are modified so that the width of varied portion 704 of trace 702 is varied symmetrically about line 716. In some embodiments, the width of varied portion 704 may be varied so that at least one of upper bound 712 and lower bound 710 diverges, away from line 716 over a first period of time and converges toward line 716 over a second period of time. For example, for a first period during which a confidence assessment associated with the physiological parameter is decreasing, at least one of upper bound 712 and lower bound 710 may diverge with respect to line 716, and for a second period during which the confidence assessment is increasing, at least one of upper bound 712 and lower bound 710 may converge with respect to line 716. In the example, at least one of upper bound 712 and lower bound 710 may diverge proportionately with the decreasing confidence assessment, and at least one of the upper bound 712 and lower bound 710 may converge proportionately with the increasing confidence assessment. In some embodiments, at least one of upper bound 712 and lower bound 710 may be modified in real-time. For example, plot 700 may be an illustration of a single snapshot of a display of trace 702 for a particular window of time 708, and the display may be, for example, a scrolling display, so that trace 702 may be continuously displayed over time, and the width of trace 702 may be varied dynamically by modifying upper bound 712 and/or lower bound 710 in real-time. In some embodiments, the width of varied portion 704 of trace 702 is varied by modifying at least one of a distance associated with the upper bound and a distance associated with the lower bound, where the distance is the vertical distance between line 716 and respective upper bound 712 or lower bound 710. In some embodiments, the width of varied portion 704 of trace 702 is varied by modifying a distance associated with the upper and lower bounds, where the distance is the vertical distance between upper bound 712 and lower bound 710. In some embodiments, a distance between the upper bound 712 and lower bound 710 is varied based at least in part on a distance parameter.

Figure 8:
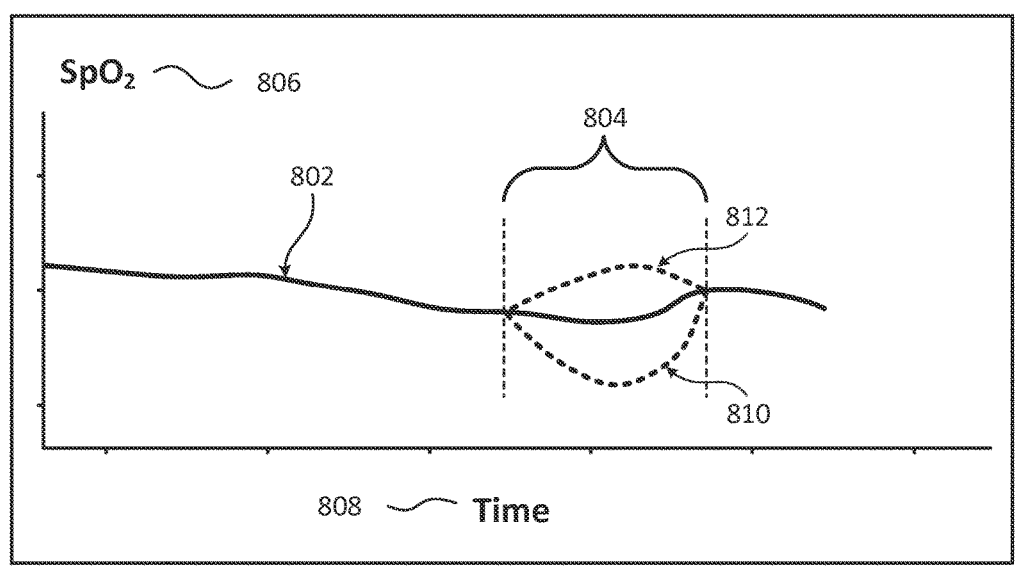
FIG. 8 shows an illustrative plot of a trace of a physiological parameter in accordance with some embodiments of the present disclosure.

FIG. 8 shows an illustrative plot 800 of a trace 802 of a physiological parameter in accordance with some embodiments of the present disclosure. Vertical axis 806 of plot 800 corresponds to oxygen saturation and horizontal axis 808 corresponds to time. Trace 802 is depicted with varied portion 804 of varying width along its length. For clarity, varied portion 804 of trace 802 is shown with a varied width that corresponds to the varied width of varied portion 504 of trace 502, shown in FIG. 5, varied portion 604 of trace 602, shown in FIG. 6, and varied portion 704 of trace 702, shown in FIG. 7. Trace 802 is depicted as including upper bound 812 and lower bound 810. Upper bound 812 and lower bound 810 define the varied width of varied portion 804 of trace 802, such that upper bound 812 and lower bound 810 form a perimeter of varied portion 804. Varied portion 804 of trace 802 is shown with upper bound 812 and lower bound 810 of varying styles along the length of trace 802.

In some embodiments, a style associated with a trace of a physiological parameter is varied based at least in part on a style parameter. In some embodiments, varying a style of displayed trace 802 includes varying a style of one or both of upper bound 812 and lower bound 810. Styles that can be varied may include, for example, a weight of a line, the continuity of a line, including whether it is represented as dotted, dashed, or solid line and the respective lengths of the dots or dashes composing the line, any other suitable style, and any combination thereof. In the embodiment shown in plot 800, upper bound 812 and lower bound 810 are varied such that each is represented by short dashes. In some embodiments, the foregoing characteristics, including, for example, width, color, and translucence, may be varied in the space between upper bound 812 and lower bound 810. In some embodiments, varying a style associated with a trace may include varying a style of line 716 of FIG. 7.

It will be understood that the particular plots shown in FIGS. 5-8 are merely exemplary and are presented as non-limiting illustrations.

Figure 9:
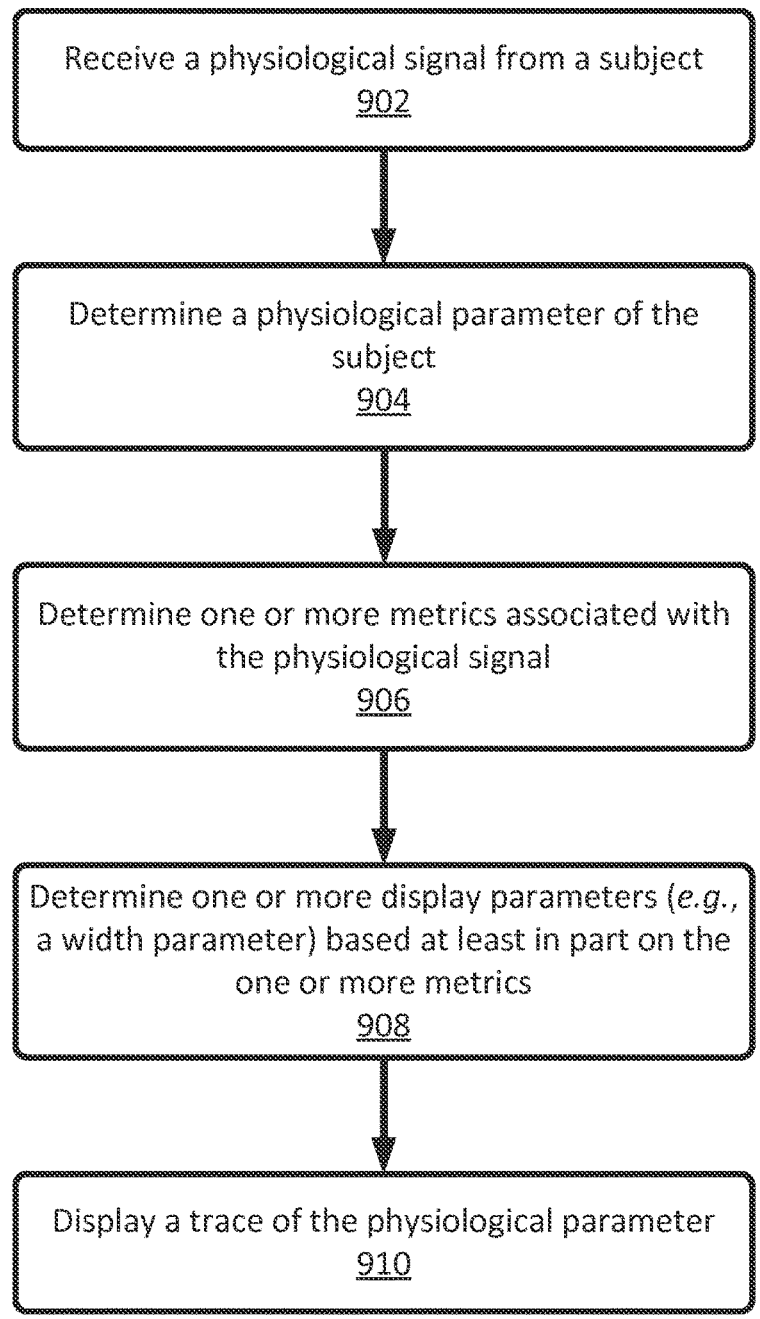
FIG. 9 shows an illustrative flow diagram including steps for displaying a trace of a physiological parameter in accordance with some embodiments of the present disclosure.

FIG. 9 shows an illustrative flow diagram 900 including steps for displaying a trace of a physiological parameter in accordance with some embodiments of the present disclosure.

Step 902 may include processing equipment receiving a physiological signal from a subject. In some embodiments, the physiological signal corresponds to an optical light signal attenuated by a subject. In some embodiments, a light detector such as detector 140 of FIG. 1 may receive the physiological signal. A light detector may detect light signals generated by light emitters that may have been partially attenuated by a subject before being detected. It will be understood that any suitable light detector or combination of light detectors may be used to detect the attenuated light signal. The amount of attenuation may correspond to, in the example of a pulse oximeter, a volume of blood or other tissue through which the light has travelled. In some embodiments, a monitor such as monitor 104 of FIG. 1 may receive the physiological signal. In some embodiments, processing equipment such as back end processing circuitry 170 of FIG. 1 may receive the physiological signal. In some embodiments, the received physiological signal may have undergone signal processing before being received, such as any suitable band-pass filtering, adaptive filtering, closed-loop filtering, any other suitable filtering, or any combination thereof. In some embodiments, signal processing may be performed on the physiological signal after it has been received. It will be understood that the processing equipment may receive any suitable physiological signal, and it is not limited to receiving an optical light signal.

Step 904 may include processing equipment determining a physiological parameter of the subject. In some embodiments, one or more physiological parameters of the subject are computed based at least in part on the received physiological signal. The physiological parameters may include, for example, one or more of blood oxygen saturation (e.g., arterial, venous, or both), pulse rate, respiration rate, respiration effort, blood pressure, hemoglobin concentration (e.g., oxygenated, deoxygenated, and/or total), any other suitable physiological parameters, or any combination thereof. Determining physiological parameters may include applying filters, transforming, performing ratio-of-ratio calculations, peak finding, demultiplexing, amplifying, performing any other suitable techniques, or any combination thereof. For example, referring back to FIG. 4, oxygen saturation 416 and pulse rate 418 are determined based at least in part on the received pleth signal 404.

Step 906 of FIG. 9 may include processing equipment determining one or more metrics associated with the physiological signal. Metrics may include, for example, any suitable measure or combination of measures for quantifying uncertainty, quality, data integrity, signal-to-noise ratio, accuracy, reliability, artifact, or interference from nearby equipment, ambient light, or otherwise, associated with the received physiological signal or the determined physiological parameter. In some embodiments, the one or more metrics may form a confidence assessment associated with the physiological signal or physiological parameter. For example, a statistical measure of uncertainty may be a metric associated with a physiological parameter and a signal quality measure may be a metric associated with a physiological signal. In some embodiments, determining a statistical measure of uncertainty may be based at least in part on known uncertainties associated with equipment, random and systematic errors, the variability among multiple determined values of a physiological parameter, any other suitable technique for computing experimental uncertainty, error propagation techniques for estimating uncertainty from component parts of a measurement, any other suitable technique for computing uncertainty, or any combination thereof. Some embodiments of step 906 are further discussed with reference to FIG. 10.

Figure 10:
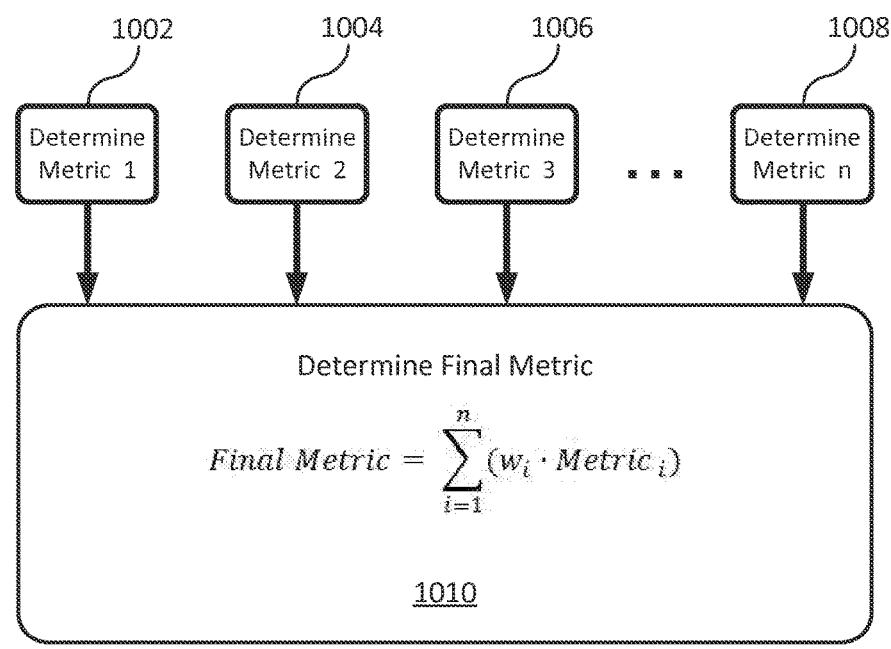
FIG. 10 shows an illustrative flow diagram including steps for determining one or more metrics associated with a physiological signal in accordance with some embodiments of the present disclosure.

FIG. 10 shows an illustrative flow diagram 1000 including steps for determining one or more metrics associated with a physiological signal in accordance with some embodiments of the present disclosure. Steps 1002, 1004, 1006, and 1008 of FIG. 10 may include processing equipment determining any specified number of metrics, 1-n. In some embodiments, metrics 1-n may include any of the metrics determined in step 906 of FIG. 9. Step 1010 may include processing equipment determining a final metric based on metrics 1-n. In some embodiments, the final metric may be indicative of a confidence assessment of the physiological signal and/or determined physiological parameter. In some embodiments, the final metric is used to determine one or more display parameters. Step 1010 depicts illustrative Equation 1 for combining metrics 1-n using a weighted summation, where w is a weight assigned to each metric:

$$\text{Final Metric} = \sum_{i=1}^{n} (w_i \cdot \text{Metric}_i) \quad (1)$$

It will be understood that Equation 1 is merely illustrative and metrics 1-n may be combined in any suitable way to determine a final metric. For example, the processing equipment may determine the final metric using a neural network, a polynomial equation, relative maximums, relative minimums, any other suitable technique, or any combination thereof. In some embodiments, a relative maximum or relative minimum may be determined from a comparison of the determined values of metrics 1-n and the final metric may be determined by setting the final metric equal to the relative maximum or relative minimum of the n metrics.

In some embodiments, one of metrics 1-n is selected as the final metric. In some embodiments, metrics 1-n may be compared to one or more metric thresholds. In an example, metric 1 may be the only metric that exceeds a metric threshold, and thus, metric 1 may be selected as the final metric. In another example, metrics 2 and 4 may both exceed a metric threshold, and thus, metrics 2 and 4 may be combined, using any of the foregoing techniques for combining metrics to determine a final metric.

Referring back to FIG. 9, step 908 may include processing equipment determining one or more display parameters based at least in part on the one or more metrics. As discussed above, with respect to step 906, metrics may include, for example, any suitable measure or combination of measures for quantifying uncertainty, quality, data integrity, signal-to-noise ratio, accuracy, reliability, artifact, or interference from nearby equipment, ambient light, or otherwise, associated with the received physiological signal or the determined physiological parameter. Display parameters may include, for example, a width parameter, a color parameter, a translucence parameter, a style parameter, a distance parameter, any other suitable parameter associated with at least one modifiable characteristic of the display, or any combination thereof. In some embodiments, a display parameter may be determined based at least in part on a combination of one or more metrics associated with the physiological signal. In some embodiments, the processing equipment may update a previously determined display parameter based on one or more new metrics. For example, the processing equipment may update a previously determined width parameter based at least in part on one or more newly received metrics and display the trace based at least in part on the updated width parameter. In another example, the processing equipment may modify at least one of the upper bound and lower bound associated with the width of a previously displayed trace based at least in part on the updated width parameter. In some embodiments, a display parameter may be determined based at least in part on a comparison of one or more metrics and one or more respective metric thresholds. In some embodiments, the processing equipment may determine a width parameter based at least in part on an uncertainty metric. When the uncertainty metric is less than a respective metric threshold, the processing equipment may determine the width parameter to be a minimum value, corresponding to a minimum width of the trace. When the uncertainty metric is greater than the respective metric threshold, the processing equipment may determine the width parameter to be a value greater than the minimum value. For example, the value of the width parameter may be determined based on the amount by which the uncertainty metric exceeds the respective metric threshold. In some embodiments, the width parameter may vary linearly or non-linearly based on the amount by which the uncertainty metric exceeds the respective metric threshold. In some embodiments, the processing equipment may determine a translucence parameter based at least in part on a signal quality metric. For example, when the signal quality metric is low, the processing equipment may vary the translucence of a trace of the physiological parameter such that it is nearly opaque and the line representing the determined physiological parameter values (e.g., line 716 of FIG. 7) may be occluded from view. In some embodiments, the one or more metrics may form a confidence assessment, as discussed above with reference to step 906, and the width parameter may vary proportionately with the confidence assessment. For example, when the confidence assessment is increasing, indicating an increasing confidence in the physiological parameter, the processing equipment may decrease the width of displayed trace by an amount proportionate to the increase in the confidence assessment. The foregoing is merely illustrative and any suitable metrics or combination of metrics may be used to determine any suitable display parameters or combinations of display parameters. Some embodiments of step 908 are further discussed with reference to FIG. 11.

Figure 11:
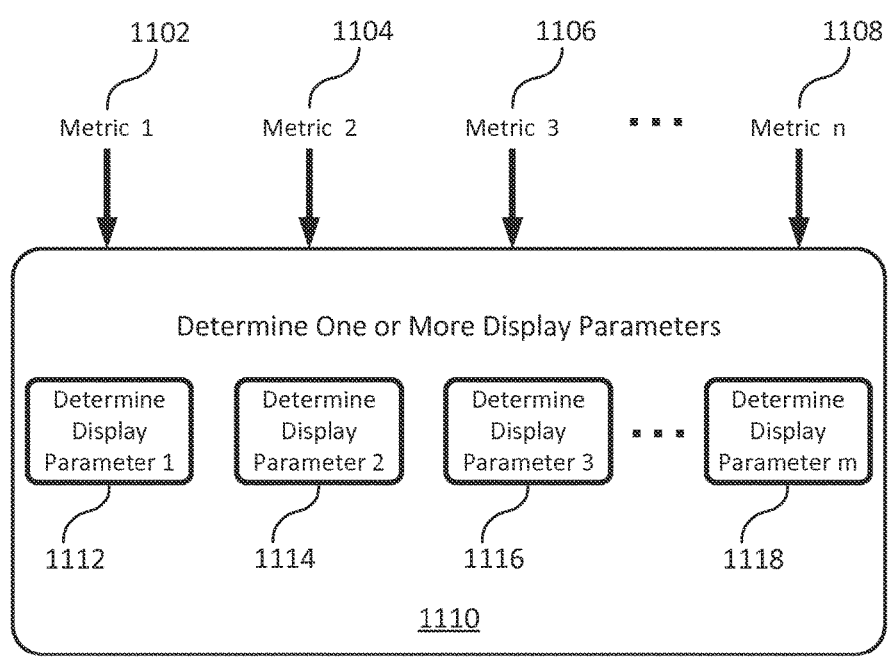
FIG. 11 shows an illustrative block diagram for determining one or more display parameters in accordance with some embodiments of the present disclosure.

FIG. 11 shows an illustrative block diagram 1100 for determining one or more display parameters in accordance with some embodiments of the present disclosure. Processing block 1110 may be implemented using any suitable processing equipment including, for example, back end processing circuitry 170 of monitor 104, shown in FIG. 1. Processing block 1110 may receive any specified number of n metrics. As depicted, processing block receives metrics 1102, 1104, 1106, and 1108. In some embodiments, metrics 1102, 1104, 1106, and 1108 may be any of the metrics determined in step 906 of FIG. 9. Processing block 1110 may include modules 1112, 1114, 1116, and 1118 for determining any specified number of display parameters, 1-m. In some embodiments, display parameters 1-m may include any of the display parameters determined in step 908 of FIG. 9. In some embodiments, processing block 1110 may combine metrics 1102, 1104, 1106, and 1108 to form a final metric, which may be used by modules 1112, 1114, 1116, and 1118 to determine display parameters 1-m, as described with reference to step 1010 of FIG. 10. In some embodiments, display parameters 1-m may be determined based at least in part on the values of metrics 1102, 1104, 1106, and 1108. In some embodiments, the severity of the value of each of metrics 1102, 1104, 1106, and 1108 may be used to determine display parameters 1-m in modules 1112, 1114, 1116, and 1118. In some embodiments, a comparison between metrics 1102, 1104, 1106, and 1108 and one or more metric thresholds may be used to determine display parameters 1-m in modules 1112, 1114, 1116, and 1118. In some embodiments, each of metrics 1102, 1104, 1106, and 1108 may be used to determine a different display parameter in modules 1112, 1114, 1116, and 1118. In an example, a width parameter may be determined in module 1112 based at least in part on metric 1, a color parameter in module 1114 based at least in part on metric 2, a translucence parameter in module 1116 based at least in part on metric 3, and a style parameter in module 1118 based at least in part on metric 4. In some embodiments, metrics 1102, 1104, 1106, and 1108 may be used to identify an artifact event, as discussed above in detail with regard to FIG. 6. In some embodiments, display parameters 1-m may be selected based on user input. In some embodiments, display parameters 1-m may be used to vary the display of the trace so as to highlight a particular metric, artifact event, other suitable physiological event, or any combination thereof. For example, the width parameter may be indicative of artifact associated with the physiological signal, and the display may be varied based on the width parameter to highlight the artifact.

Referring back to FIG. 9, step 910 may include processing equipment displaying a trace of the physiological parameter based at least in part on the one or more display parameters. In some embodiments, the trace may be displayed on display 184 of FIG. 1, display 328 of multi-parameter physiological monitor 326 or display 320 of monitor 314 of FIG. 3, or any other suitable display for depicting physiological information. In some embodiments, displaying a trace of a physiological parameter includes displaying the trace, in real-time or from historical data, using, for example, a scrolling display, a dynamically updating display, any other suitable display for displaying physiological data, and any combination thereof. Displaying the trace may be based at least in part on one or more of the display parameters, including, a width parameter, a color parameter, a translucence parameter, a style parameter, a distance parameter, any other suitable parameter for varying the display of a trace, or any combination thereof. In an example, displaying a trace based at least in part on a width parameter may correspond to displaying a trace of varying width along its length, as described in detail with respect to plot 500 of FIG. 5. In another example, displaying a trace based at least in part on a width parameter and a color parameter may correspond to displaying a trace of varying width along its length and of varying at least one color associated with the trace, as described in detail with respect to plot 600 of FIG. 6. An optional step, not shown, includes the processing equipment storing physiological information, including data related to the physiological parameter, trace, metrics, display parameters, and a graphical representation of the varied display of the trace over time.

It will be understood that the steps above are exemplary and that in some implementations, steps may be added, removed, omitted, repeated, reordered, modified in any other suitable way, or any combination thereof.

The foregoing is merely illustrative of the principles of this disclosure, and various modifications may be made by those skilled in the art without departing from the scope of this disclosure. The above-described embodiments are presented for purposes of illustration and not by way of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed:

1. A system for displaying physiological information, the system comprising:
    an input configured to receive a physiological signal from a subject;
    a display; and
    one or more processors configured to:
        determine a physiological parameter of the subject based at least in part on the received physiological signal;

determine one or more metrics associated with the physiological parameter;

determine a width parameter based at least in part on the one or more metrics;

present, via the display, a trace of the physiological parameter, wherein a length of the trace extends along a first axis and a width of the trace is measured along a second axis orthogonal to the first axis; and vary the width of the presented trace along the length of the trace based at least in part on the width parameter, wherein the width represents a range of values of the physiological parameter at a particular time.

2. The system of claim 1, wherein the received physiological signal is a photoplethysmograph signal.

3. The system of claim 1, wherein the physiological parameter is selected from the group consisting of: oxygen saturation, respiration rate, and pulse rate.

4. The system of claim 1, wherein the one or more processors are configured to vary the width of the trace by at least varying the range of values of the physiological parameter.

5. The system of claim 4, wherein the one or more processors are configured to vary the width of the trace by at least varying the width of the trace in real time.

6. The system of claim 4, wherein the one or more metrics comprise a statistical measure of uncertainty associated with the physiological parameter, and wherein the one or more processors are configured to vary the width of the presented trace by at least increasing the width of the trace when the uncertainty associated with the physiological parameter increases.

7. The system of claim 4, wherein the one or more metrics comprise a signal quality measure associated with the received physiological signal, and wherein the one or more processors are configured to vary the width of the presented trace by at least increasing the width of the trace when the signal quality measure associated with the received physiological signal decreases.

8. The system of claim 4, wherein the one or more metrics comprise a confidence assessment associated with the physiological parameter, and wherein the one or more processors are configured to proportionately vary the width of the presented trace with the confidence assessment.

9. The system of claim 4, wherein the one or more processors are further configured to vary at least one color of the trace.

10. The system of claim 4, wherein the one or more processors are further configured to vary a translucence of the trace.

11. The system of claim 4, wherein the range of values of the physiological parameter comprises an upper bound and a lower bound, the upper bound and the lower bound defining the width of the trace, and wherein the one or more processors are configured to vary the width of the trace by modifying at least one of the upper bound or the lower bound.

12. The system of claim 11, wherein the one or more processors are configured to modify the at least one of the upper bound or the lower bound by at least modifying the at least one of the upper bound or the lower bound in real-time.

13. The system of claim 11, wherein the one or more processors are configured to modify the at least one of the upper bound or the lower bound by at least:

updating a previously determined width parameter based on one or more newly received metrics; and modifying the at least one of the upper bound or the lower bound of the width of a previously presented trace based at least in part on the updated width parameter.

14. The system of claim 11, wherein the trace comprises a line associated with the determined physiological parameter, and wherein the one or more processors are configured to present the trace of the physiological parameter by presenting, via the display, the line, the upper bound, and the lower bound, such that the presented line is distinct from the presented upper bound and the presented lower bound.

15. The system of claim 14, wherein the one or more processors are configured to vary the width of the trace by modifying the at least one of the upper bound or the lower bound such that the width of the trace is varied asymmetrically about the presented line.

16. The system of claim 14, wherein the one or more metrics comprise a confidence assessment associated with the physiological parameter, and wherein the one or more processors are configured to modify the at least one of the upper bound or the lower bound by at least:

modifying the at least one of the upper bound or the lower bound such that the at least one of the upper bound or the lower bound diverges away from the presented line over a first period of time during which the confidence assessment is decreasing; and modifying the at least one of the upper bound or the lower bound such that the at least one of the upper bound or the lower bound converges toward the presented line over a second period of time during which the confidence assessment is increasing.

17. The system of claim 16, wherein the at least one of the upper bound or the lower bound diverges proportionately with the decreasing confidence assessment and the at least one of the upper bound or the lower bound converges proportionately with the increasing confidence assessment.

18. The system of claim 11, wherein the one or more processors are configured to vary the width of the trace by at least modifying the upper bound and the lower bound at the same time.

19. The system of claim 1, wherein the width parameter is indicative of artifact associated with the physiological signal.

20. The system of claim 1, wherein the one or more processors are configured to present, via the display, the trace of the physiological parameter by at least presenting, via the display, the trace having the width that varies over time.

21. A system for displaying physiological information, the system comprising:

processing circuitry configured for:

receiving a physiological signal from a subject;

determining a physiological parameter of the subject based at least in part on the received physiological signal;

determining one or more confidence metrics associated with the physiological parameter;

determining a width parameter based at least in part on the one or more confidence metrics; and displaying a trace of the physiological parameter, wherein a length of the trace extends along a time axis and a width of the trace is measured in a direction orthogonal to the time axis; and varying the width of the displayed trace of the physiological parameter along the length of the trace based at least in part on the width parameter, wherein the width of the trace indicates a range of values of the physiological parameter at a particular time.

22. The system of claim 21, wherein the received physiological signal is a photoplethysmograph signal, and wherein the physiological parameter is selected from the group consisting of: oxygen saturation, respiration rate, and pulse rate.

23. The system of claim 21, wherein the width parameter comprises a measure of width of the trace of the physiological parameter, and wherein the processing circuitry is configured for varying the width of the trace based at least in part on the measure of width in real time.

24. The system of claim 23, wherein:
the range of values of the physiological parameter comprises an upper bound and a lower bound, the upper bound and the lower bound defining the width of the trace,
the trace comprises a line associated with the determined physiological parameter, and
the processing circuitry is configured for continuously presenting, via the display, the trace by at least presenting the line, the upper bound, and the lower bound, such that the presented line is distinct from the presented upper bound and the presented lower bound.

* * * * *